United States Patent
Müller et al.

(10) Patent No.: US 10,317,444 B2
(45) Date of Patent: Jun. 11, 2019

(54) SENSOR AND METHOD FOR DETERMINING A DIELECTRIC PROPERTY OF A MEDIUM

(71) Applicant: SIEMENS AKTIENGESELLSCHAFT, München (DE)

(72) Inventors: Dominikus Joachim Müller, Eichenau (DE); Florian Poprawa, München (DE); Abdellatif Zanati, München (DE)

(73) Assignee: Siemens Aktiengesellschaft, München (DE)

( * ) Notice: Subject to any disclaimer, the term of this patent is extended or adjusted under 35 U.S.C. 154(b) by 320 days.

(21) Appl. No.: 14/777,270

(22) PCT Filed: Mar. 13, 2014

(86) PCT No.: PCT/EP2014/054919
§ 371 (c)(1),
(2) Date: Sep. 15, 2015

(87) PCT Pub. No.: WO2014/140151
PCT Pub. Date: Sep. 18, 2014

(65) Prior Publication Data
US 2016/0025787 A1 Jan. 28, 2016

(30) Foreign Application Priority Data
Mar. 15, 2013 (DE) .................. 10 2013 204 586

(51) Int. Cl.
*G01R 27/28* (2006.01)
*G01N 22/00* (2006.01)
*G01R 27/26* (2006.01)

(52) U.S. Cl.
CPC ............ *G01R 27/28* (2013.01); *G01N 22/00* (2013.01); *G01R 27/2647* (2013.01)

(58) Field of Classification Search
CPC . G01R 27/2617; G01R 27/28; G01R 27/2647
See application file for complete search history.

(56) References Cited

U.S. PATENT DOCUMENTS

| 4,651,085 A | 3/1987 | Sakurai et al. |
| 5,219,827 A | 6/1993 | Higaki et al. |

(Continued)

FOREIGN PATENT DOCUMENTS

| CN | 1206840 A | 2/1999 |
| CN | 1353812 A | 6/2002 |

(Continued)

OTHER PUBLICATIONS

Chngjun Liu et al, "A Microstrip Resonator With Slotted Ground Plane for Comples Permittivity Mearsurements of Liquids," IEEE Microwave and Wireless Components Letters, IEEE Service Center, New York, NY, vol. 18, No. 4, pp. 257-259, ISSN: 1531-1309, DOI: 10.1009/LMWC.2008.918894, XP011347340, 2008.

(Continued)

*Primary Examiner* — Jeff W Natalini
(74) *Attorney, Agent, or Firm* — Lempia Summerfield Katz LLC

(57) ABSTRACT

The invention relates to a sensor (300) for determining a dielectric property of a medium (205). The sensor (300) has a substrate (301, 302), which has at least one via (203, 204), and a waveguide (12), which is arranged so as to be planar in relation to an upper surface of the substrate (301). The waveguide (12) can be connected to an analysis device (20) by means of the at least one via (203, 204). Furthermore, the waveguide (12) is designed to receive an input signal from the analysis device (20) and to output an output signal to the (Continued)

analysis device (20). When of the waveguide (12) is in contact with a medium (205), properties of the input signal and of the output signal are indicative of the dielectric property of the medium (205). The arrangement of the waveguide (12) so as to be planar in relation to the substrate (301) enables larger measurement ranges and improved measurement accuracies. Furthermore, a compact construction is achieved by the planar structure. The invention further relates to a sensor arrangement and a method for determining a dielectric property of a medium by means of a sensor.

14 Claims, 3 Drawing Sheets

(56) References Cited

U.S. PATENT DOCUMENTS

| | | | |
|---|---|---|---|
| 5,229,726 | A | 7/1993 | Kent |
| 5,334,941 | A | 8/1994 | King |
| 5,389,875 | A | 2/1995 | Rosen et al. |
| 6,411,103 | B1 | 6/2002 | Tobias et al. |
| 7,075,314 | B2 | 7/2006 | Ehata |
| 7,468,645 | B2 | 12/2008 | Yamaguchi et al. |
| 2003/0016032 | A1 | 1/2003 | Licini et al. |

FOREIGN PATENT DOCUMENTS

| | | |
|---|---|---|
| CN | 1534303 A | 10/2004 |
| CN | 102590230 A | 7/2012 |
| DE | 3412704 A1 | 10/1984 |
| DE | 19925468 A1 | 12/2000 |
| DE | 19943701 A1 | 5/2001 |
| DE | 102010019525 B4 | 6/2012 |
| DE | 102009024203 B4 | 1/2013 |
| EP | 1703275 A1 | 9/2006 |
| GB | 2202947 A | 10/1988 |
| JP | H03286601 A | 12/1991 |
| JP | H04506404 A | 11/1992 |
| JP | H07507396 A | 8/1995 |
| JP | 2001083102 A | 3/2001 |
| JP | 2005217199 A | 8/2005 |
| WO | WO9100512 A1 | 1/1991 |
| WO | WO02067774 A1 | 9/2002 |

OTHER PUBLICATIONS

German Office Action for related German Application No. 10 2013 204 586.7, dated Jul. 19, 2013, with English Translation.
PCT International Search Report and Written Opinion of the International Searching Authority dated Feb. 16, 2015 for corresponding PCT/EP2014/054919.
PCT International Search Report and Written Opinion of the International Searching Authority dated Jun. 27, 2014 for corresponding PCT/EP2014/054919.
PCT International Search Report and Written Opinion of the International Searching Authority dated May 12, 2015 for corresponding PCT/EP2014/054919.
Chinese Office Action for related Chinese Application No. 201480015953.3 dated Nov. 2, 2016, with English Translation.
English Translation of Japanese Notice of Rejection for related Japanese Application No. 2015-562141 dated Sep. 31, 2016.
Japanese Office Action for Japanese Application No. 2015-562141, dated Jun. 2, 2017, with English Translation.
European Search Report for European Patent Application No. 14711197.5-1003, dated Mar. 19, 2018.
Folgerø, Kjetil, et al. "Permittivity measurement of thin liquid layers using open-ended coaxial probes." Measurement Science and Technology 7.8 (1996): 1164.
Ghasr, Mohammad Tayeb, et al. "Comparison of near-field millimeter-wave probes for detecting corrosion precursor pitting under paint." IEEE Transactions on Instrumentation and Measurement 54.4 (2005): 1497-1504.

SENSOR AND METHOD FOR DETERMINING A DIELECTRIC PROPERTY OF A MEDIUM

The present invention relates to a sensor and a method for determining a dielectric property of a medium. Furthermore, the invention relates to a sensor arrangement comprising such a sensor and an analysis device.

In various technical fields it may be necessary to determine one or more dielectric properties of a medium. Such a determination can be carried out with the aid of microwaves, for example, wherein various methods can be used, such as, for example, a transmission measurement, reflection measurement or resonance measurement. In the case of the transmission measurement, dielectric properties are determined on the basis of the transmission of signals through a medium or a conductor. In the case of the reflection measurement, dielectric properties are determined on the basis of the reflection of signals at or by means of the medium. The resonance measurement is based on the determination of the resonance properties, that is to say the oscillation properties, of the medium, which can in turn be used for determining the dielectric properties.

The results of these measurements can be used for determining dielectric properties of the medium, in particular the complex dielectric constant. Said properties can provide information about various other properties of the medium. These include, for example, the concentration of glucose, alcohol or salt in a medium.

The determination of the dielectric constant may be desired in various fields, such as in medicine or in industrial installations, for example in the context of process instrumentation. In this case, it is desirable to be able to ascertain even small changes in concentration, which necessitates a high measurement accuracy.

Accordingly, it is an object of the present invention to improve the determination of dielectric properties of a medium with regard to the measurement accuracy.

Accordingly, a sensor for determining a dielectric property of a medium is proposed. The sensor comprises a substrate, which has at least one plated-through hole, and a waveguide, which is arranged in a planar manner in relation to an upper surface of the substrate. The waveguide is connectable to an analysis device via the at least one plated-through hole. Furthermore, the waveguide is designed to receive an input signal from the analysis device and to output an output signal to the analysis device, wherein properties of the input signal and of the output signal when the waveguide is in contact with a medium are indicative of the dielectric property of the medium.

Transmission and reflection measurements can be carried out with the proposed sensor. An improvement of the measurement accuracy of the dielectric property of the medium is achieved by virtue of the planar structure of said sensor. Furthermore, compact measuring units can be realized, as a result of which the sensor is useable in a multiplicity of technical fields. Since the sensor can have small dimensions, it can also be used in a mobile manner. The sensor can be used for example in the medical field as a mobile appliance which can carry out measurements even directly on a person, wherein the medium could correspond to skin. Sampling can therefore be obviated.

Furthermore, the sensor can be used in various industrial installations, either as a permanently installed device or as a mobile device. In this case, the sensor canlikewise be brought directly into contact with the medium, as a result of which sampling can be obviated.

In the sensor described, a waveguide is arranged in a planar manner in relation to a substrate. A printed circuit board, for example, can be used as the substrate. The substrate can consist of a dielectric material or comprise the latter.

The waveguide can be any type of waveguide which can be arranged in a planar manner in relation to the upper surface of the substrate. In this context, "in a planar manner in relation to the upper surface of the substrate" can mean in a planar manner on or in a planar manner with the upper surface of the substrate. A planar waveguide is preferably involved. A compact sensor unit can be achieved by virtue of the planar arrangement. "Planar" should be understood to mean an arrangement of the waveguide in which the upper surface of the sensor arrangement is level or flat.

The waveguide is connectable to an analysis device via plated-through holes. In this context, plated-through holes denote openings which extend through the substrate from the upper surface of the substrate to the opposite side of the substrate.

The analysis device can be any desired device suitable for transmitting an input signal to the waveguide, for receiving an output signal from the latter and for determining a dielectric property of the medium on the basis of properties of these two signals. The determination can be carried out for example on the basis of a comparison of the phase and/or amplitude of the input signal and of the output signal, since these vary in a material-dependent manner, that is to say depending on the medium.

A signal which is transmitted through the waveguide generates a leakage field around the waveguide. This (electromagnetic) leakage field permeates the medium. In this case, for example, the phase and/or amplitude of the input and output signals change. These changes can be used for determining the dielectric property(-ies) of the medium.

The input signal is generated by the analysis device. If the measurement to be carried out is a transmission measurement, the input signal is fed into the waveguide at one end of the waveguide and is received again by the analysis device as output signal at the other end of the waveguide. In the case of a reflection measurement, the input signal is fed into the waveguide at one end. At the other end, which in this case is open, that is to say is not electrically connected, the signal enters the medium from the waveguide and is at least partly reflected by said medium and fed back into the waveguide. This fed-back signal is in turn received by the analysis device as output signal.

The analysis device can be a network analyzer, for example. Such a network analyzer can be a vectorial network analyzer (VNA). The latter can be used to measure scattering parameters of electrical measurement objects. Scattering parameters denote the reflection and transmission properties of the measurement objects. In connection with the sensor described herein, the term "measurement object" relates to a medium. The medium can assume a solid, liquid or gaseous state. In this case, a liquid or a gas can be involved, inter alia.

The sensor described herein therefore provides a cost-effective device for determining dielectric properties of a medium. This device offers a determination of the dielectric properties over a large measurement range. The sensor can be used without sampling and is therefore simpler than conventional sensors in terms of handling.

In one embodiment, the waveguide is arranged in a planar manner on the upper surface of the substrate.

In accordance with this embodiment, the waveguide is a planar waveguide arranged on the upper surface of the substrate. In this context, planar means that the waveguide is flat and together with the substrate forms a level surface.

In a further embodiment, the waveguide is a stripline.

A stripline can be a microstrip line, a coplanar line or a slotted line. Other types of striplines or other planar waveguides are also possible. These types of waveguides afford the advantage that they can be arranged in a planar manner on a substrate such as, for example, a conventional printed circuit board. Striplines usually consist of one or more thin, conductive strips applied on a dielectric (for example a substrate).

In a further embodiment, the substrate has at least two plated-through holes, and the waveguide is connectable to an input terminal and an output terminal of the analysis device via the at least two plated-through holes.

In this way, the waveguide can be connected to the analysis device by both of its ends. In this case, the analysis device can be a two-port analysis device. This arrangement is used for transmission measurement in which an input signal is fed into one end of the waveguide by the analysis device and an output signal is received at the other end of the waveguide. As soon as the waveguide is in contact with the medium to be examined, that is to say is "loaded", the properties of the output signal vary in comparison with the input signal. By way of example, the so-called scattering parameters (S-parameters) can be determined. These S-parameters are measured as a function of frequency and indicate values of the reflection and transmission. From these it is possible to determine the dielectric properties of the medium, such as the dielectric constant, for example, by means of suitable methods.

In a further embodiment, one end of the waveguide is arranged in a planar manner with the substrate.

In this embodiment, the waveguide is arranged such that only one end of the waveguide is arranged at the upper surface of the substrate, and the waveguide extends through the plated-through hole. The end of the waveguide at the upper surface of the substrate is arranged in a planar manner with the substrate.

In a further embodiment, the waveguide is embodied as an open conductor.

An open conductor, that is to say a conductor which is coupled to the analysis device only by one end, whereas the other end has no electrical connection, is used for reflection measurement, as described above. A signal which is fed into the waveguide emerges from the waveguide at the open end. The signal is at least partly fed back into the waveguide again by the medium to be examined. S-parameters can likewise be determined on the basis of this feedback. The network analyzer can be embodied as a single-port system in this case.

In a further embodiment, the substrate comprises a dielectric material.

The substrate can be a printed circuit board consisting of a dielectric material.

In a further embodiment, a protective layer is arranged above the upper surface of the substrate.

Such a protective layer can serve for protection against contamination or against moisture as a result of the medium. The protective layer can be a film, for example. By way of example, Parylene C or silicone can be used as material for the protective layer. These materials can be used over a high temperature range. Other materials can likewise be used. Preferably, said materials should not influence the radio-frequency properties of the waveguide. The protective layer can be very thin, for example a few micrometers thick, for example in the range of 5 to 10 micrometers, which likewise contributes to the radio-frequency properties of the waveguide not being influenced.

In a further embodiment, the substrate has a lower substrate layer and an upper substrate layer.

Both substrate layers can be produced from the same material. The analysis device can be integrated in the lower substrate layer.

In a further embodiment, a ground layer is arranged between the upper substrate layer and the lower substrate layer.

The ground layer separates the upper substrate layer from the lower substrate layer. A connection to ground is made possible by the ground layer if plated-through holes do not extend through the entire substrate, but rather only through a substrate layer as far as the ground layer. The ground layer can consist of a metal or comprise a metallization.

In a further embodiment, the waveguide is connected to a further waveguide on the lower substrate layer via a coaxial junction.

A coaxial junction denotes a broadband junction, that is to say a connection, between the waveguide and a further waveguide or some other conductor. That means that the waveguide is connectable to the analysis device via broadband junctions. Broadband junctions afford the transmission of a wide frequency range. Coaxial junctions are used for this purpose. These junctions are provided by means of a coaxial conductor having an inner conductor and a further conductor arranged concentrically around the latter. Said further conductor can consist of a plurality of individual conductors. This arrangement provides a broadband (as a result of the coaxial junction) and multilayered (as a result of the plurality of waveguides) junction.

Furthermore, a sensor arrangement for determining a dielectric property of a medium is proposed. The sensor arrangement comprises the sensor explained above and an analysis device connected to the sensor.

In one development, the analysis device is integrated in the substrate of the sensor.

The analysis device can be integrated directly into the substrate. In this case, the waveguide is situated on one side of the sensor arrangement and the analysis device is situated on the opposite side of the sensor arrangement. In this way, firstly, a compact sensor arrangement can be achieved. Secondly, it is possible for only the side of the sensor arrangement which has the waveguide to be brought into contact with the medium, such that the analysis device is protected.

In a further development, the analysis device is a network analyzer.

A network analyzer (VNA) is used in radio-frequency engineering to measure the scattering parameters (S-parameters), that is to say reflection and transmission, of electrical measurement objects (here the medium) as a function of frequency.

The network analyzer can transmit a signal (outgoing wave) into the waveguide that is in contact with the object to be examined (device under test), that is to say the medium. The frequency, amplitude and phase of the signal are known. The medium reflects a part of said signal (returning wave at the input), which part constitutes the output signal in the case of the reflection measurement. The rest of the signal, that is to say the non-reflected signal, passes into the waveguide in the medium, is altered (for example damped, amplified or phase-shifted), and is received again by the network analyzer at the output of the waveguide as transmitted signal (returning wave at the output). The differences between the input signal and the output signal are used for determining the dielectric properties of the medium, as described above.

In addition, a method for determining a dielectric property of a medium by means of a sensor is proposed. The sensor comprises a substrate, which has at least one plated-through hole, and a waveguide, which is arranged in a planar manner in relation to an upper surface of the substrate, wherein the waveguide is connectable to an analysis device via at least one plated-through hole. The method comprises, as a first step, receiving an input signal from the analysis device. In a further step, an output signal is output to the analysis device, wherein properties of the input signal and of the output signal when the waveguide is in contact with a medium are indicative of the dielectric property of the medium.

The above-described properties, features and advantages of this invention and the way in which they are achieved will become clearer and more clearly understood in association with the following description of the exemplary embodiments which are explained in greater detail in association with the drawings.

In this case:

In the figures, identical or functionally identical elements have been provided with the same reference signs, unless indicated otherwise.

Figure 1:
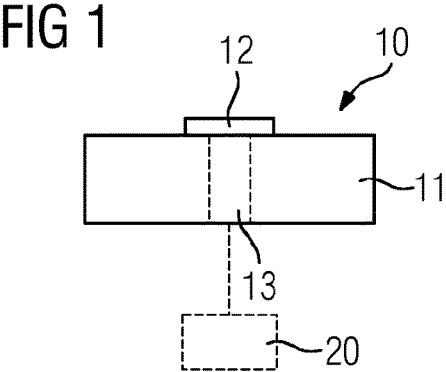
FIG. 1 shows a schematic view of one exemplary embodiment of a sensor for determining a dielectric property of a medium.

FIG. 1 shows one exemplary embodiment of a sensor 10 for determining a dielectric property of a medium. The sensor 10 comprises a substrate 11, wherein a waveguide 12 is arranged in a planar manner in relation to the substrate 11 on an upper surface of the substrate 11.

In a planar manner in relation to the substrate 11 can mean both planar on the upper surface of the substrate 11 and planar with the substrate 11. This is explained in even greater detail in the following figures. Although the waveguide 12 projects beyond the substrate 11 for illustration purposes in FIG. 1, the upper surface of the substrate 11 together with the waveguide 12 is substantially level.

The waveguide can be connected to an analysis device 20, for example a network analyzer, via a plated-through hole 13. The vectorial network analyzer (VNA) 20 transmits a signal to the waveguide 12, or couples a signal into the waveguide 12, and receives a signal from the waveguide 12. On the basis of these signals, the VNA 20 can determine a dielectric property of a medium that is brought into contact with the sensor 10. A reflection measurement can be carried out with the sensor 10.

Figure 2:
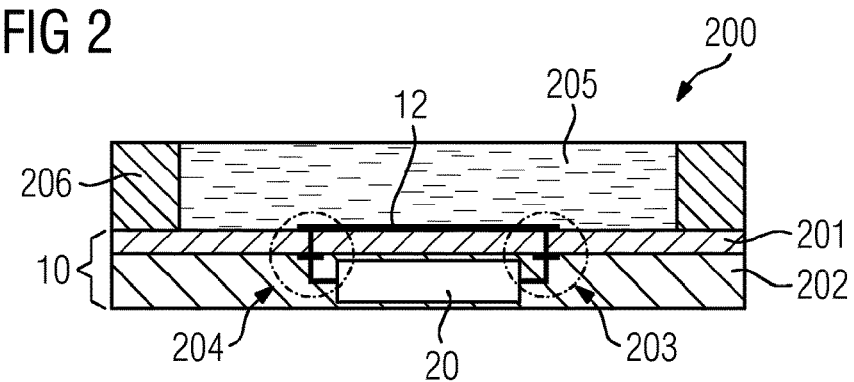
FIG. 2 shows a schematic view of a first exemplary embodiment of a sensor arrangement for determining a dielectric property of a medium.

One example of an arrangement for a transmission measurement is shown in FIG. 2. The sensor 10 in the sensor arrangement 200 comprises two substrate layers, an upper substrate layer 201 and a lower substrate layer 202. The waveguide 12 is brought into contact with a medium 205, for example a liquid in a container 206. The container 206 can be chosen with a size such that it has no influence on the measurement.

The waveguide 12 is connected to the VNA 20 via multilayered broadband junctions 203, 204. The sensor 10 can be produced cost-effectively on commercially available substrates, such as printed circuit boards. The VNA 20 can be integrated in the lower substrate layer 202, as shown in FIG. 2. Alternatively, the VNA 20 can also be arranged externally. However, an integral construction affords a particularly compact sensor arrangement.

Figure 3:
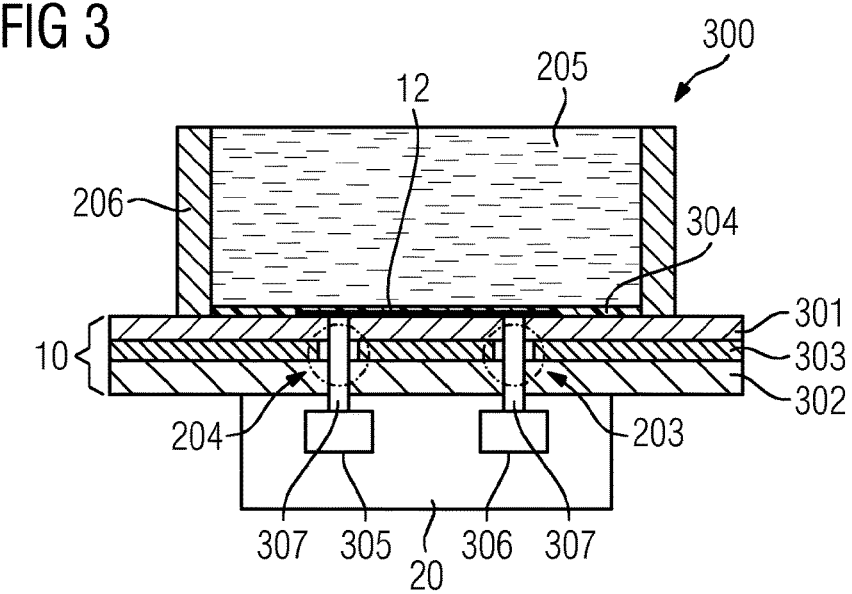
FIG. 3 shows a schematic view of a second exemplary embodiment of a sensor arrangement for determining a dielectric property of a medium.

As is evident in the sensor arrangement 300 from FIG. 3, the VNA 20 for the measurement of discrete frequencies can be a two-port network analyzer having two ports 305, 306. In order to be able to determine even small changes in concentration of, for example, alcohol, salt or sugar content in the medium 205, a high measurement accuracy is desirable, which can be achieved by the embodiments of the sensor and of the sensor arrangement as described herein. The ports 305, 306 are connected to the waveguide 12 via connections 307, for example cables, through the plated-through holes.

As shown in FIG. 3, a protective layer 304, for example a film, can be fitted above the sensor 10 in order to increase the robustness of the sensor 10. Said protective layer 304 protects the sensor 10 against contamination or ingress of liquid. As a result, it is also possible to prevent liquid from penetrating through the substrate 11.

In this embodiment, a ground layer 303 is arranged between the upper substrate layer 301 and the lower substrate layer 302. Said ground layer enables a connection of the upper substrate layer 301 to ground, without the connections having to be led through the lower substrate layer 302. This likewise leads to a simplified and compact sensor arrangement 300.

Figure 4:
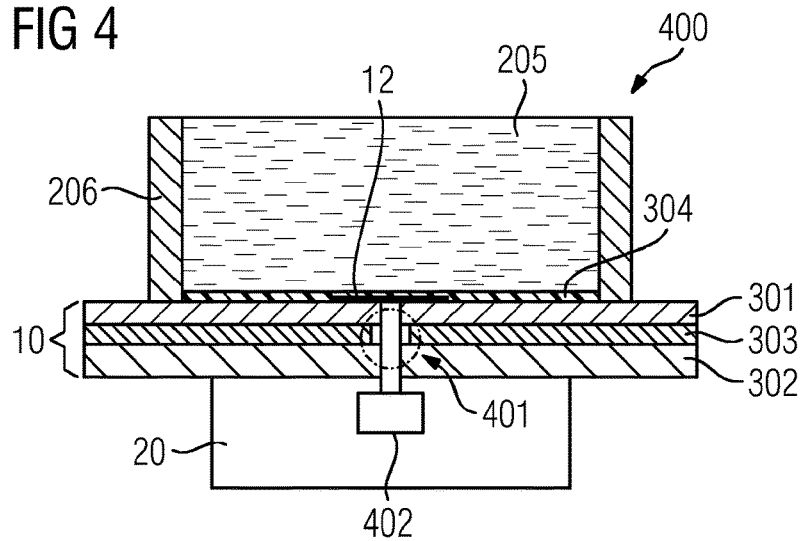
FIG. 4 shows a schematic view of a third exemplary embodiment of a sensor arrangement for determining a dielectric property of a medium.

In the case of the sensor arrangement 400 in FIG. 4, the waveguide 12 is arranged in a planar manner with the upper surface of the upper substrate layer 301. One end of the waveguide 12 therefore terminates with the upper surface. The waveguide 12 is connected to a port 402 of the VNA 20, which is a single-port network analyzer in this case, via a coaxial junction 401.

A further waveguide (not shown here), for example a microstrip line, can be situated on the underside of the lower substrate layer 302. This is transferred into an open conductor through the coaxial junction 401.

Figure 5:
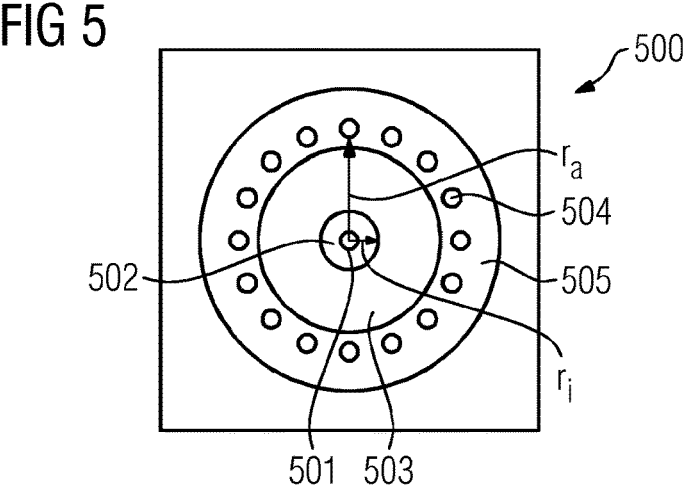
FIG. 5 shows a schematic plan view of one exemplary embodiment of a coaxial junction for a sensor according to FIG. 1 or for a sensor arrangement according to any of FIGS. 2 to 4.

FIG. 5 shows such a coaxial junction 500. The latter can be used to connect two waveguides to one another or a waveguide 12 to the VNA 20. A central conductor 501 provides a plated-through hole from the upper substrate layer 301 to the lower substrate layer. With a thickness $r_i$ (internal radius), the central conductor is surrounded by an insulation layer 502. A second insulation layer 503 surrounds the latter. A third insulation layer 505 in turn surrounds the second insulation layer 503. The insulation layers 502, 503, 505 are arranged concentrically around the central conductor 501. Plated-through holes 504 that provide a connection to the ground layer are arranged in the third insulation layer 505.

Figure 6:
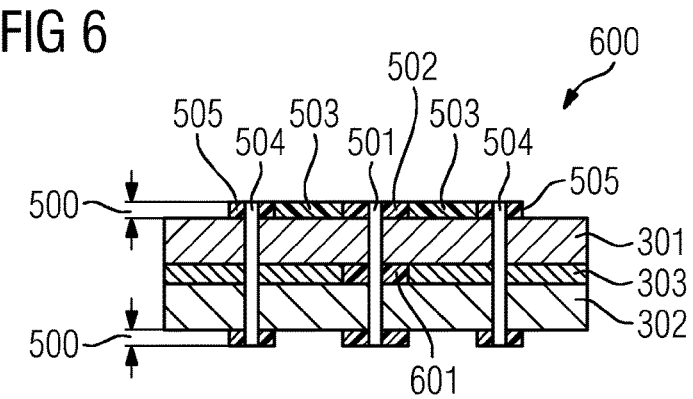
FIG. 6 shows a schematic side view of one exemplary embodiment of a coaxial junction for a sensor according to FIG. 1 or for a sensor arrangement according to any of FIGS. 2 to 4.

As shown in FIG. 6, the plated-through holes 504 extend only as far as the ground layer 303. In FIG. 6, a first waveguide 500 is arranged on the upper substrate layer 301 and a second waveguide 500 is arranged on the lower substrate layer 302. The two waveguides 500 are connected to one another via the central conductor 501 of the coaxial junction. The central conductor 501 is electrically isolated from the ground layer 303 by an insulation layer 601 or cutout.

Figure 7:
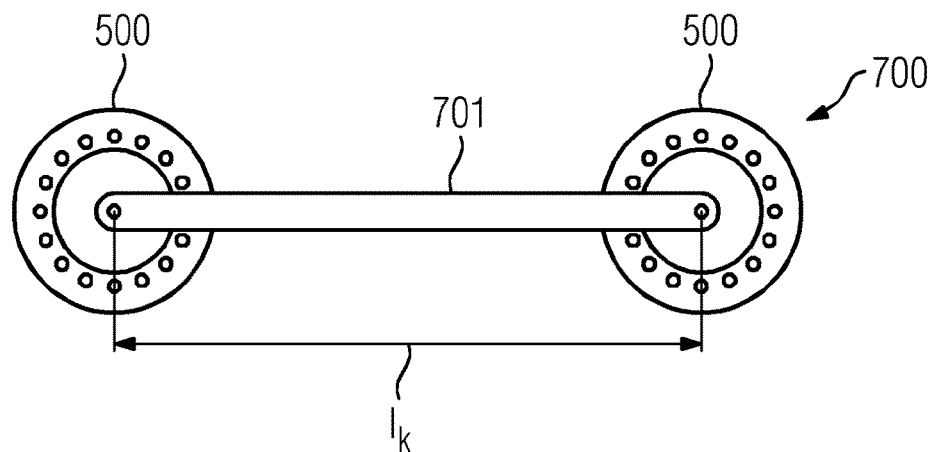
FIG. 7 shows a schematic plan view of one exemplary embodiment of a coaxial junction for a sensor according to FIG. 1 or for a sensor arrangement according to either of FIGS. 2 and 3.

In the case of a sensor arrangement 300 for a transmission measurement, as shown in FIG. 3, for example, the waveguide 12 is connected to the VNA 20 via plated-through holes. FIG. 7 shows a coaxial junction 700 for such a sensor. The two coaxial junctions 500 shown are connected by the microstrip line 701, or some other waveguide. The coupling length $l_k$ of the coaxial junctions, that is to say the length of the microstrip line, can be chosen depending on the measurement frequencies and the medium 205 to be examined, in order to achieve optimum waveguiding. The choice of the radii $r_i$ and $r_a$ can influence the sensitivity of the measurements.

Figure 8:
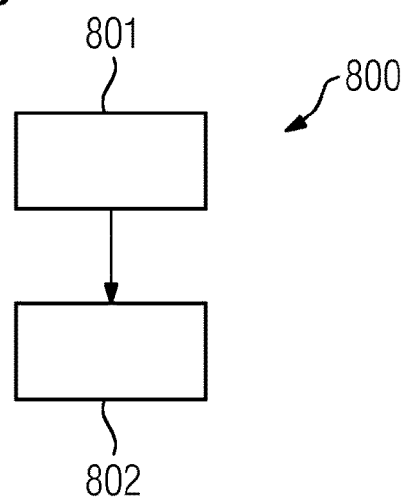
FIG. 8 shows a schematic flow diagram of one example of a method for determining a dielectric property of a medium.

FIG. 8 shows a schematic flow chart of a method 800 for determining a dielectric property of a medium 205. In this case, in a first step 801, a waveguide 12 of a sensor 10 such as was described in FIGS. 1 to 7 receives an input signal from an analysis device 20. In a second step 802, the waveguide 12 outputs an output signal to the analysis device 20. If the waveguide 12 is in contact with a medium 205, properties of the input signal and of the output signal are indicative of the dielectric property of the medium 205. Said property can be determined and used further, as described above.

As already described, the sensor described herein and the corresponding sensor arrangement are cost-effective to produce in comparison with known sensors. The sensors can be used and integrated in a simple manner in different measurement environments. The sensitivity of the measurements can be set by appropriate choice of the radii $r_i$ and $r_a$ of the coaxial junctions. Furthermore, a compact measuring apparatus can be realized by virtue of the planar construction, since sensor and analysis device can form one unit. In addition, larger measurement ranges and improved measurement accuracies are made possible.

Although the invention has been more specifically illustrated and described in detail by means of the preferred exemplary embodiments, nevertheless the invention is not restricted by the examples disclosed, and other variations can be derived therefrom by the person skilled in the art, without departing from the scope of protection of the invention.

The invention claimed is:

1. A sensor for determining a dielectric property of a medium, the sensor comprising:
a substrate having at least one plated-through hole, an upper substrate layer, a lower substrate layer, and a ground layer, wherein each substrate layer of the upper substrate layer and the lower substrate layer comprises a same dielectric material, and wherein the ground layer is arranged between the upper substrate layer and the lower substrate layer, and
a waveguide arranged in a planar manner in relation to an upper surface of the substrate,
wherein the waveguide is connectable to an analysis device via the at least one plated-through hole,
wherein the waveguide is configured to receive an input signal from the analysis device and to output an output signal to the analysis device, wherein properties of the input signal and the output signal when the waveguide is in contact with a medium are indicative of the dielectric property of the medium.

2. The sensor as claimed in claim 1, wherein the waveguide is arranged in a planar manner on the upper surface of the substrate.

3. The sensor as claimed in claim 1, wherein the waveguide is a stripline.

4. The sensor as claimed in claim 1, wherein the substrate comprises at least two plated-through holes, and wherein the waveguide is connectable to an input terminal and an output terminal of the analysis device via the at least two plated-through holes.

5. The sensor as claimed in claim 4, wherein a protective layer is arranged above the upper surface of the substrate.

6. The sensor as claimed in claim 5, wherein the waveguide is connected to a further waveguide on the lower substrate layer via a coaxial junction.

7. The sensor as claimed in claim 1, wherein one end of the waveguide is arranged in a planar manner with the substrate.

8. The sensor as claimed in claim 7, wherein the waveguide is embodied as an open conductor.

9. The sensor as claimed in claim 1, wherein a protective layer is arranged above the upper surface of the substrate.

10. The sensor as claimed in claim 1, wherein the waveguide is connected to a further waveguide on the lower substrate layer via a coaxial junction.

11. A sensor arrangement for determining a dielectric property of a medium, the sensor arrangement comprising:
a sensor, comprising:
a substrate having at least one plated-through hole, an upper substrate layer, a lower substrate layer, and a ground layer, wherein each substrate layer of the upper substrate layer and the lower substrate layer comprises a same dielectric material, and wherein the ground layer is arranged between the upper substrate layer and the lower substrate layer, and
a waveguide arranged in a planar manner in relation to an upper surface of the substrate, wherein the waveguide is connectable to an analysis device via the at least one plated-through hole, and wherein the waveguide is configured to receive an input signal from the analysis device and to output an output signal to the analysis device, wherein properties of the input signal and the output signal when the waveguide is in contact with a medium are indicative of the dielectric property of the medium; and
an analysis device connected to the sensor.

12. The sensor arrangement as claimed in claim 11, wherein the analysis device is integrated in the substrate of the sensor.

13. The sensor arrangement as claimed in claim 11, wherein the analysis device is a network analyzer.

14. A method for determining a dielectric property of a medium by a sensor, wherein the sensor comprises a substrate having at least one plated-through hole, an upper substrate layer, a lower substrate layer, and a ground layer, wherein each substrate layer of the upper substrate layer and lower substrate layer comprises a same dielectric material, and wherein the ground layer is arranged between the upper substrate layer and the lower substrate layer, and a waveguide arranged in a planar manner in relation to an upper surface of the substrate, wherein the waveguide is connectable to an analysis device via the at least one plated-through hole, the method comprising:

receiving an input signal from the analysis device, and outputting an output signal to the analysis device, wherein properties of the input signal and of the output signal when the waveguide is in contact with a medium are indicative of the dielectric property of the medium.

* * * * *